US011517260B2

(12) United States Patent
Workman et al.

(10) Patent No.: US 11,517,260 B2
(45) Date of Patent: Dec. 6, 2022

(54) FETAL HEALTH DATA MONITORING

(71) Applicant: OWLET BABY CARE, INC., Lehi, UT (US)

(72) Inventors: Kurt G. Workman, Provo, UT (US); Daniela Turner, Provo, UT (US); Ali Carlile, Vineyard, UT (US); Ethan Lawrence, Kaysville, UT (US); Paul Allen, Saratoga Springs, UT (US); Zack Bomsta, Provo, UT (US); Ryan Workman, Draper, UT (US); Bruce Olney, Grantsville, UT (US); Sean Kerman, Orem, UT (US); Ajay Iyer, Murray, UT (US)

(73) Assignee: Owlet Baby Care, Inc., Lehi, UT (US)

( * ) Notice: Subject to any disclaimer, the term of this patent is extended or adjusted under 35 U.S.C. 154(b) by 529 days.

(21) Appl. No.: 15/476,295

(22) Filed: Mar. 31, 2017

(65) Prior Publication Data
US 2017/0281087 A1    Oct. 5, 2017

Related U.S. Application Data

(60) Provisional application No. 62/430,783, filed on Dec. 6, 2016, provisional application No. 62/317,180, filed on Apr. 1, 2016.

(51) Int. Cl.
*A61B 5/00*    (2006.01)
*A61B 5/0205*    (2006.01)
(Continued)

(52) U.S. Cl.
CPC .......... *A61B 5/6804* (2013.01); *A61B 5/0205* (2013.01); *A61B 5/02411* (2013.01);
(Continued)

(58) Field of Classification Search
CPC ... A61B 5/0205; A61B 5/6804; A61B 5/0402; A61B 5/1115; A61B 5/1118
See application file for complete search history.

(56) References Cited

U.S. PATENT DOCUMENTS 4,781,200 A    11/1988  Baker
5,033,864 A    7/1991   Lasecki et al.
(Continued)

FOREIGN PATENT DOCUMENTS

CA       2885972       12/2014
CN       101790346 A    7/2010
(Continued)

OTHER PUBLICATIONS

International Search Report and Written Opinion issued in PCT/US2017/025563 dated Jun. 21, 2017.
(Continued)

*Primary Examiner* — Lynsey C Eiseman
*Assistant Examiner* — Amanda L Steinberg
(74) *Attorney, Agent, or Firm* — Workman Nydegger P.C.

(57) ABSTRACT

A system for monitoring fetal health data and mother health data comprises a belly-covering garment that is configured to at least partially cover a belly and to hold one or more sensor modules directly adjacent to the belly. One or more sensor modules disposed within the belly-covering garment. The one or more sensor modules comprise a pulse-oximeter sensor that gathers pulse oximetry data from the mother through contact with the belly. The one or more sensor modules also comprise an accelerometer sensor that gathers movement data from the mother. Additionally, the one or more sensor modules comprise a fetal sensor that gathers health data from a fetus within the belly.

16 Claims, 6 Drawing Sheets

(51) Int. Cl.
*A61B 8/08* (2006.01)
*A61B 5/11* (2006.01)
*A61B 8/02* (2006.01)
*A61B 5/024* (2006.01)
*A61B 5/1455* (2006.01)
*A61B 7/04* (2006.01)
*A61B 5/0402* (2006.01)
*A61B 8/00* (2006.01)
*A61B 5/318* (2021.01)

(52) U.S. Cl.
CPC .......... *A61B 5/1118* (2013.01); *A61B 5/4362* (2013.01); *A61B 5/6823* (2013.01); *A61B 8/02* (2013.01); *A61B 8/0866* (2013.01); *A61B 8/488* (2013.01); *A61B 5/14552* (2013.01); *A61B 5/318* (2021.01); *A61B 5/7225* (2013.01); *A61B 7/04* (2013.01); *A61B 8/4227* (2013.01); *A61B 8/4416* (2013.01); *A61B 8/4472* (2013.01); *A61B 2503/02* (2013.01); *A61B 2562/0219* (2013.01)

(56) References Cited

U.S. PATENT DOCUMENTS

| | | |
|---|---|---|
| 5,842,982 A | 12/1998 | Mannheimer |
| 5,954,663 A | 9/1999 | Gat |
| 6,047,201 A | 4/2000 | Jackson |
| 6,102,856 A | 8/2000 | Groff et al. |
| 6,454,708 B1 | 9/2002 | Ferguson et al. |
| 6,498,652 B1 | 12/2002 | Varshneya et al. |
| 6,569,095 B2 | 5/2003 | Eggers |
| 7,949,389 B2 | 5/2011 | Wolfberg et al. |
| 8,094,013 B1 | 1/2012 | Lee et al. |
| 8,275,436 B2 * | 9/2012 | Wang ............... A61B 5/1464 600/324 |
| 8,340,748 B2 | 12/2012 | Kimura et al. |
| 8,347,144 B2 | 1/2013 | Khalak et al. |
| 8,417,351 B2 | 4/2013 | Kilger |
| 8,620,448 B1 | 12/2013 | Delia |
| 8,666,481 B2 | 3/2014 | Harrold et al. |
| 8,781,847 B2 | 7/2014 | Simms et al. |
| 9,028,405 B2 | 5/2015 | Tran |
| 9,314,159 B2 | 4/2016 | Lyon et al. |
| 9,579,055 B1 | 2/2017 | Rood et al. |
| 9,585,614 B2 | 3/2017 | Dugan |
| 9,763,583 B2 | 9/2017 | Oz et al. |
| 9,763,616 B2 | 9/2017 | Dugan |
| 2002/0133067 A1 | 9/2002 | Jackson |
| 2003/0158593 A1 | 8/2003 | Heilman et al. |
| 2008/0275349 A1 | 11/2008 | Halperin et al. |
| 2009/0247849 A1 | 10/2009 | McCutcheon et al. |
| 2010/0168596 A1 | 7/2010 | Jaeschke et al. |
| 2010/0191154 A1* | 7/2010 | Berger ............... A61B 5/742 600/595 |
| 2010/0241018 A1 | 9/2010 | Vogel |
| 2010/0274104 A1 | 10/2010 | Khan |
| 2011/0160591 A1* | 6/2011 | Smith ............... A61B 8/02 600/453 |
| 2011/0288379 A1 | 11/2011 | Wu |
| 2012/0209088 A1 | 8/2012 | Romem |
| 2012/0232398 A1 | 9/2012 | Roham et al. |
| 2012/0232416 A1 | 9/2012 | Gilham et al. |
| 2012/0253142 A1 | 10/2012 | Meger et al. |
| 2012/0299732 A1 | 11/2012 | Vogel |
| 2013/0021154 A1 | 1/2013 | Solomon et al. |
| 2013/0072765 A1 | 3/2013 | Kahn et al. |
| 2013/0102856 A1 | 4/2013 | Wolfberg |
| 2013/0102857 A1* | 4/2013 | Wolfberg ............... A61B 5/344 600/382 |
| 2013/0197362 A1 | 8/2013 | Mittal et al. |
| 2013/0289361 A1 | 10/2013 | Bridge et al. |
| 2014/0228653 A1 | 8/2014 | Kiraly et al. |
| 2015/0150538 A1 | 6/2015 | Reuter et al. |
| 2015/0164438 A1 | 6/2015 | Halperin et al. |
| 2015/0201846 A1 | 7/2015 | Maiershon et al. |
| 2015/0250419 A1 | 9/2015 | Cooper et al. |
| 2016/0081567 A1 | 3/2016 | Nousiainen et al. |
| 2016/0120500 A1 | 5/2016 | Myklebust et al. |
| 2016/0157717 A1* | 6/2016 | Gaster ............... A61B 5/0444 600/301 |
| 2016/0183873 A1 | 6/2016 | Lin et al. |
| 2016/0317091 A1 | 11/2016 | Olukoya et al. |
| 2016/0374608 A1* | 12/2016 | Dugan ............... A61B 5/1114 600/301 |
| 2017/0127995 A1 | 5/2017 | Hyde et al. |
| 2017/0127996 A1 | 5/2017 | Hyde et al. |
| 2017/0127997 A1 | 5/2017 | Hyde et al. |
| 2017/0265799 A1 | 9/2017 | Du et al. |

FOREIGN PATENT DOCUMENTS

| | | | |
|---|---|---|---|
| CN | 103260528 A | 8/2013 | |
| CN | 103845060 A | 6/2014 | |
| CN | 104305992 A | 1/2015 | |
| CN | 104382585 A | 3/2015 | |
| CN | 105208924 A | 12/2015 | |
| CN | 105228512 A | 1/2016 | |
| CN | 105997059 A | 10/2016 | |
| CN | 106999100 A | 8/2017 | |
| CN | 107260177 A | 10/2017 | |
| EP | 1432349 B1 * | 6/2006 | ........... A61B 5/0011 |
| EP | 1854403 A2 | 11/2007 | |
| WO | 2004075750 A1 | 9/2004 | |
| WO | 2009146181 A1 | 12/2009 | |
| WO | 2011039745 A1 | 4/2011 | |
| WO | 201252904 A1 | 4/2012 | |
| WO | 201359267 A2 | 4/2013 | |
| WO | 201402823 A1 | 1/2014 | |
| WO | 2014162135 | 10/2014 | |
| WO | 2014162135 A1 | 10/2014 | |
| WO | 2015062851 | 5/2015 | |
| WO | 2015082987 | 6/2015 | |
| WO | 201667276 A1 | 5/2016 | |
| WO | 201793251 A1 | 6/2017 | |
| WO | 2017102566 A1 | 6/2017 | |
| WO | 2017142277 A1 | 8/2017 | |

OTHER PUBLICATIONS

M.J. Rooijakkers et al. "Influence of Electrode Placement on Signal Quality for Ambulatory Pregnancy Monitoring," Computational and Mathematical Methods in Medicine vol. 2014 pp. 1-12.

European Search Report issued in Application No. EP17776853 dated Jul. 22, 2019.

Communication under Rule 71(3) EPC received for European Patent Application No. 17776853.8, dated Mar. 9, 2021, 6 pages.

Office Action received for Chinese Patent Application No. 201780021795, dated Dec. 3, 2020, 12 pages (Original Document Only).

Decision to grant a European patent received for European Application No. 17776853.8, dated Jun. 10, 2021, 2 pages.

European Search Report and Search Opinion Received for EP Application No. 17776853.8, dated Jul. 30, 2019, 14 pages.

* cited by examiner

FETAL HEALTH DATA MONITORING

CROSS-REFERENCE TO RELATED APPLICATIONS

This application claims priority to and the benefit of U.S. Provisional Application Ser. No. 62/317,180 entitled "FETAL BIOMETRIC MONITORING", filed on Apr. 1, 2016 and U.S. Provisional Application Ser. No. 62/430,783 entitled "FETAL BIOMETRIC MONITORING", filed on Dec. 6, 2016. The entire content of each of the aforementioned applications is incorporated by reference herein in its entirety.

BACKGROUND

Every year, within the United States, around one percent of all pregnancies end with a stillborn child. The causes of many of these stillbirths are unknown. While various risk factors have been identified with stillbirths, many times the actual cause of the stillbirth is not known unless an autopsy, or some other investigative procedure, is performed on the stillborn child.

To combat stillbirths and to identify potential problems early in a pregnancy, frequent maternity visits with a doctor are suggested. These visits often involve taking health measurements of both the mother and the unborn child. Through monitoring these health measurements (i.e., "vital signs"), a trained medical professional can track the health of both the baby and the mother, and potentially identify developing problems before they become irreversible.

Unfortunately, even with the wide availability of advanced medical care and associated maternity care, many stillbirths continue to occur. As such, there are many problems within the field that remain unsolved.

BRIEF SUMMARY

Disclosed embodiments include a system for monitoring fetal health data and/or mother health data. The system can comprise a belly-covering garment that is configured to at least partially cover a belly and to hold one or more sensor modules directly adjacent to the belly. The system can also comprise one or more sensor modules disposed within the belly-covering garment. The one or more sensor modules can comprise a pulse-oximeter sensor that gathers pulse oximetry data from the mother through contact with the belly. The one or more sensor modules can also comprise an accelerometer sensor that gathers movement data from the mother. Additionally, the one or more sensor modules can also comprise a fetal sensor that gathers health data from a fetus within the belly.

Additionally, disclosed embodiments include a method for monitoring fetal health data and/or mother health data. The method includes receiving, from a pulse-oximeter sensor, pulse oximetry data from a mother. The method also includes receiving, from an accelerometer sensor, movement data from the mother. Further, the method includes receiving, from a fetal sensor, fetal health data from a fetus within the mother's belly. Further still, the method includes identifying a relative location of the fetus within the mother's belly using one of more of the pulse oximetry, the movement data, and the fetal health data. The pulse-oximeter sensor, the accelerometer sensor, and the fetal sensor are disposed within a belly-covering garment that is configured to at least partially cover the mother's belly and to hold one or more sensor modules directly adjacent to the belly.

Disclosed embodiments also include a system for monitoring fetal health data and/or mother health data. The system includes a garment that is configured to at least partially cover a belly and to hold a plurality of sensor modules directly adjacent to the belly. The plurality of sensor modules is disposed individually as an array of sensor modules spread across the belly. A first sensor module comprises a first electrocardiogram electrode that is configured to gather first fetal heartbeat data, wherein the first sensor module is associated with a first region of the belly. A second sensor module comprises a second electrocardiogram electrode that is configured to gather second fetal heartbeat data, wherein the second sensor module is associated with a second region of the belly that is different than the first region. A computing system is configured to determine whether the fetus is within the first region or the second region based upon readings received from the first sensor module and the second sensor module.

Additional features and advantages of exemplary implementations of the invention will be set forth in the description which follows, and in part will be obvious from the description, or may be learned by the practice of such exemplary implementations. The features and advantages of such implementations may be realized and obtained by means of the instruments and combinations particularly pointed out in the appended claims. These and other features will become more fully apparent from the following description and appended claims, or may be learned by the practice of such exemplary implementations as set forth hereinafter.

BRIEF DESCRIPTION OF THE DRAWINGS

In order to describe the manner in which the above recited and other advantages and features of the invention can be obtained, a more particular description of the invention briefly described above will be rendered by reference to specific embodiments thereof, which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF EMBODIMENTS

Disclosed embodiments comprise systems, methods, and apparatuses for monitoring fetal health data and/or mother health data. In at least one embodiment, a belly-covering garment is worn by the mother. The belly-covering garment comprises embedded sensors (also referred to herein as "sensor modules") that gather fetal health data and/or mother health data. The gathered data can be analyzed to identify potentially problematic trends or results.

The belly-covering garment may comprise a variety of different sensors positioned at different location within the belly-covering garment. For example, one or more pulse-oximeters may be positioned at different locations with the belly-covering garment. The pulse-oximeters may be used to gather pulse data from the mother. Additionally, one or more electrocardiogram ("ECG") electrodes can also be positioned at different location within the belly-covering garment. The one or more ECG electrodes may be used to gather pulse data from the fetus (also referred to herein as the "unborn baby"). In various embodiments, the data received from both the pulse-oximeters and the ECG electrodes can be used together to generates more accurate readings from both the mother and the fetus.

Accordingly, a pregnant mother can utilize an embodiment of the sensor system disclosed herein to monitor the health and progress of her unborn child and the pregnancy in general. For example, the sensor system may be able to identify the heart rate of the unborn child and the heart rate of the mother. The identified heart rate information may provide valuable information regarding the health of the unborn child and the health of the mother. Additionally, in at least one implementation, the sensor system can identify potentially negative trends in the information received from the sensor system. As such, the sensor system may provide, previously unavailable, alerts and proactive notification regarding the health of the unborn child and the mother.

Figure 1:
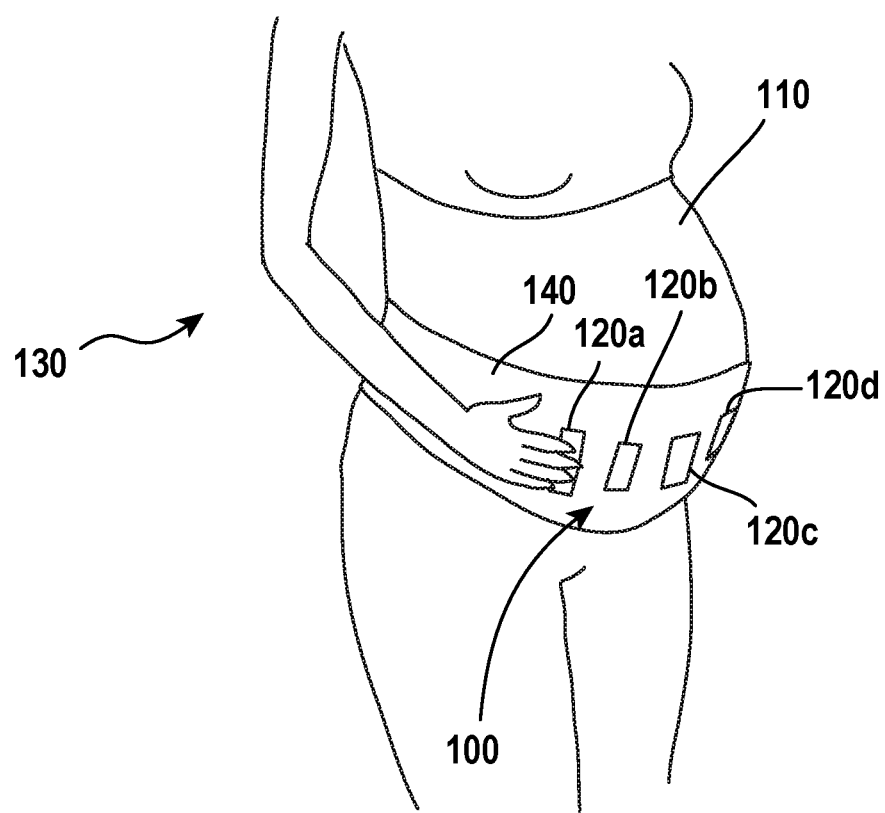
FIG. 1 depicts a front perspective view of an implementation of a sensor system in communication with an exemplary belly of a pregnant mother.

Turning now to the Figures, FIG. 1 depicts a front perspective view of a schematic diagram of an implementation of a sensor system 100 in communication with an exemplary belly 110 of a pregnant mother 130. The depicted exemplary sensor system 100 and belly 110 are depicted for the sake of clarity and explanation. For example, the depicted physical form and location of the sensor system 100 are provided only for purposes of discussion and does not necessarily limit the sensor system to any particular physical form, location, or configuration.

The sensor system 100 can comprise a belly-covering garment 140 that is configured to at least partially cover the mother's belly 110 and to hold one or more sensor modules 120(a-d) directly adjacent to the belly 110. The belly-covering garment 140 may comprise a wrap, a belt, a shirt, a strap, or any other garment that is capable of holding the sensor modules sensor modules 120(a-d) adjacent to the belly 100. In at least one embodiment, the sensor modules 120(a-d) are removable from the belly-covering garment 140 so that the belly-covering garment 140 can be washed without the sensor modules 120(a-d).

In at least one implementation, the belly-covering garment 140 comprises pockets that hold the sensor modules 120(a-d). The pockets may comprise holes, or portals, that allow at least a portion of the sensor modules 120(a-d) to be in direct contact with the skin of the mother's belly 100. For example, in at least one implementation, a pulse oximeter sensor may be positioned within the belly-covering garment 140 such that it is in direct contact with the mother's belly and is able to completely block external light. Similarly, in at least one embodiment, one or more sensor modules 120(a-d) comprise an ECG electrode. When in use, the ECG electrodes are in contact with the mother's belly 100, but in at least one embodiment, at least a portion of the ECG electrode and/or associated electronics are removable from the belly-covering garment 140.

The sensor system 100 may comprise either a single sensor module 120a or multiple sensor modules 120(a-d) disposed within the belly-covering garment 140. The sensor modules 120(a-d) can comprise a variety of different sensors and configurations. In at least one implementation, the sensor system 100 comprise twenty to thirty sensors spread between the various sensor modules 120(a-d). Each sensor module 120(a-d) may comprise the same configuration of sensors or different sensor configurations.

In at least one implementation, the sensor system 100 may comprise a pulse-oximeter sensor that gathers pulse oximetry data from the mother through contact with the belly 110. The sensor system 100 may comprise a single pulse oximeter sensor 120a or multiple pulse oximeter sensors 120(a-d) that are each capable of independently gathering pulse-oximetry data. As such, in various implementations, there may be multiple data sources capable of providing pulse oximetry data.

The sensor system 100 can also comprise one or more accelerometer sensors that gather movement data from the mother. The accelerometer sensors may comprise a single stand-alone unit 120a, or may be integrated into one or more of the sensor modules 120(a-d). For example, various accelerometer sensors 120(a-d) may be positioned around the belly-covering garment 140.

The periodic placement of accelerometer sensors 120(a-d) around the belly-covering garment 140 may allow the accelerometer sensors 120(a-d) to detect and track both the movements of the pregnant mother and the movements of the unborn baby. For example, a kick from the unborn baby may cause an accelerometer sensor nearest to the location of the kick (e.g., sensor module 120c) to register a sharp acceleration, while the other sensor modules 120a, 120b, 120d each register a more muffled acceleration. Various algorithms and pattern matching functions are used to distinguish the kick from other movements of the mother. Accordingly, the accelerometer sensors 120(a-d) track normal actions and movements of the pregnant mother and also track, over time, the movements of the unborn child.

In at least one embodiment, the sensor system 100 comprises one or more fetal sensors that gather health data from an unborn child within the womb. The fetal sensors may be positioned within a single stand-alone sensor module 120a or within sensor modules 120(a-d) disposed around the mother's belly 110. For example, the fetal sensor 120(a-d) may comprise a Doppler sensor that detects an unborn child's heartbeat. In additional or alternate embodiments, the fetal sensor 120(a-d) comprises one or more ECG electrodes, or any other sensor capable of detecting a heartbeat of an unborn child. In yet further embodiments, the fetal sensors comprise at least two sensors that are held against the mother's belly 110. One sensor may utilize ultrasonic waves to track the heartbeat of the unborn child. The other sensor may measure the duration of contractions. The sensors may comprise ultrasound, electrocardiogram ("ECG"), high sensitivity microphones, or any number of other possible sensors. In at least one embodiment, a particular sensor functions as both a fetal sensor and a pulse-oximeter sensor. Similarly, a particular sensor functions as both a fetal sensor and an accelerometer sensor.

In at least one embodiment, the data from the pulse-oximetry sensor referenced above may be used to filter out noise from the data gathered by the fetal sensor. For example, in some cases, the heartbeat of the pregnant mother may be difficult to distinguish from, or may add noise to, the detected heartbeat of the unborn child. The mother's heart beat detected by the pulse-oximeter sensor may be filtered out of the unborn child's heart beat detected by the fetal sensor. Similarly, the unborn child's heart beat detected by the fetal sensor may be filtered out of the mother's heart beat detected by the pulse-oximeter sensor.

In at least one implementation, data from both the fetal sensor and the pulse-oximeter can be stored and processed later. Processing longer time periods of data for both datasets may allow better resulting data to be calculated. For example, pattern detection algorithms can be utilized to identify patterns of the mother's heart beat in the data. The identified mother's heart beat patterns can then be removed from the data for the unborn child's heartbeat. As such, utilizing data from both sensors may create better heart rate data for both the pregnant mother and the unborn child.

Additionally, in at least one implementation, the sensor system 100 comprises a location detection sensor that detects a location of the fetus within the belly. The location detection sensor(s) comprise one or more of the above discussed sensors that are disposed within the sensor modules 120(a-d). For example, the location detection sensors may comprise the above referenced fetal sensor in the form of an ECG electrodes. In particular, each sensor module 120(a-d) may comprise an ECG electrode for detecting the heartbeat of the unborn child. In at least one embodiment, the ECG electrode feeds into a junction gate field-effect transistor ("JFET"). The JFET provides a low impedance and low noise circuit for gathering the fetal health data. The location of the unborn child can be detected by determining which location detection sensor is receiving the strongest heart beat reading.

Figure 2:
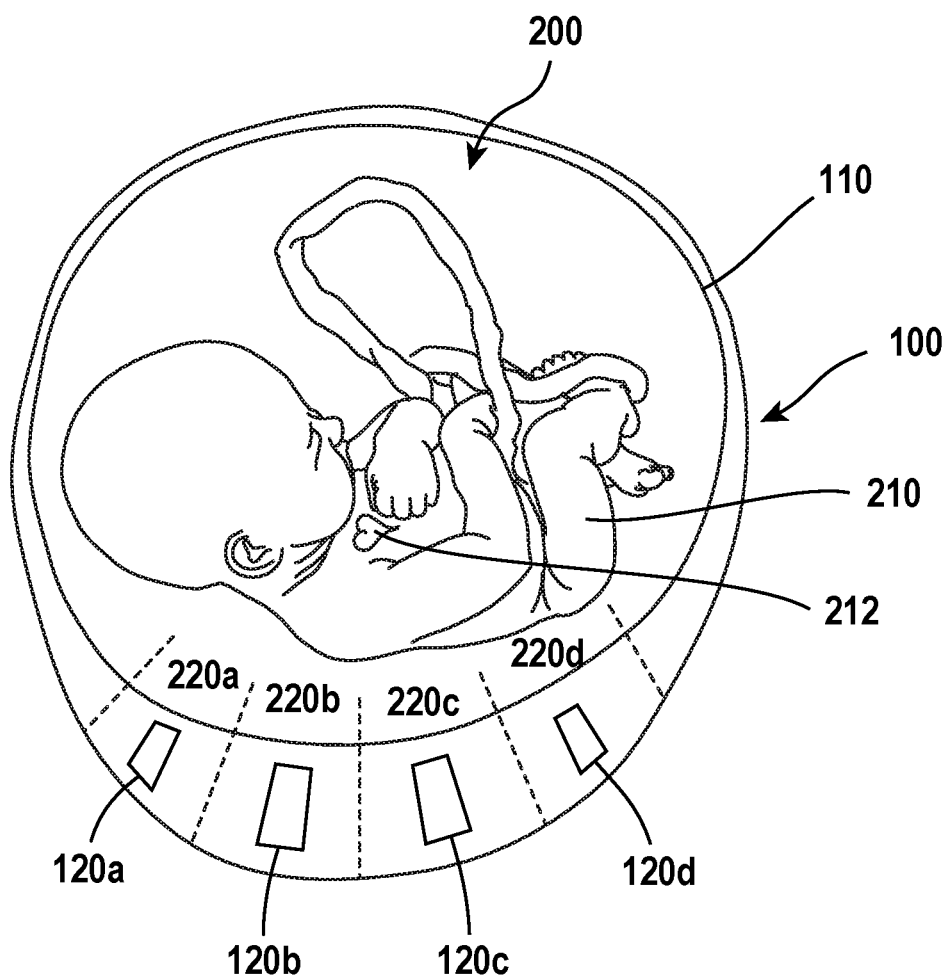
FIG. 2 depicts a top cross-sectional view of an embodiment of a sensor system in communication with an exemplary belly of a pregnant mother.

For example, FIG. 2 depicts a top cross-sectional view of an embodiment of a sensor system 100 in communication with an exemplary belly 110 of a pregnant mother. An unborn child 210 is depicted within the womb 200 of the pregnant mother. The sensor system 100 is depicted with sensor modules 120(a-d) disposed around the belly 110. While the sensor modules 120(a-d) are depicted covering only a portion of the pregnant mother's belly 110, in at least one implementation, additional sensor modules can be disposed completely around the mother such that one or more sensors are disposed adjacent to the mother's back. Additionally, while the sensor modules 120(a-d) are shown aligned with a single axis across the belly 110, in at least one embodiment, the sensors are positioned in a nonlinear, two-dimensional pattern.

In at least one implementation, the positioning of the sensor modules 120(a-d) creates sensor zones 220(a-d) within the womb 200 of the mother. The relative location of the unborn baby 210 within the womb 200 can be detected within a respective sensor zone 220(a-d). For example, sensor module 120c may comprise a Doppler sensor or an ECG electrode. The Doppler sensor or ECG electrode 120c may be receiving a stronger heart beat reading than sensor modules 120a, 120b, 120d. Accordingly, the sensor system 100 may determine that the unborn baby 210 is within sensor zone 220d because sensor module 120d can most clearly detect the unborn baby's heart 212.

One will understand that the zones 220(a-d) depicted in FIG. 2 are provided only for the sake of example and explanation. In practice, the zones may not explicitly define geometric volumes within the womb 200. Instead, the zones 220(a-d) may function more as gradients that blend into each other. In particular, the unborn baby's location within womb 200 may be determined to be more closely associated with a particular sensor 120(a-d) and hence a zone 220(a-d) that is physically associated with that sensor. Additionally, the unborn baby's location within the womb 200 may be more closely associated with the location of the unborn baby's heart 212 being within a zone 220(a-d).

Once a position of the unborn baby 210 is detected, the system 100 can manipulate the other sensor modules 120a, 120b, 120d accordingly. For example, to conserve power, the sensor system 100 can turn-off one or more sensors within each of sensing modules 120a, 120b, 120d. Similarly, the sensor system 100 can decrease the sensor sample rate of the other sensor modules 120a, 120b, 120d. For example, sensor module 120c can be configured to gather sensor data continuously, every 15 seconds, every 30 seconds, every minute, or every 5 minutes. In contrast, sensor modules 120a, 120b, 120d can be configured to gather sensor data every 15 minutes, every 30 minutes, or at a third of the frequency of sensor module 120d. Adjusting the sampling rates of the various sensor modules 120(a-d) in this fashion may save battery power, while maximizing sensor data received from the sensor module 120c closest to the unborn child 210.

In at least one implementation, the location of the unborn baby 210 within the womb 200 can be redetermined at a set interval. For example, every 15 minutes, every 30 minutes, or every hour, the sensor system 100 can sample and compare the signal strength at each sensor module 120(a-d) to determine what sensor zone 220(a-d) contains the unborn baby's heart 212. In contrast, in at least one implementation, the location of the unborn baby 210 within the womb 200 can be redetermined when the strength of the signal at sensor module 120d (or the sensor otherwise corresponding with the last detected sensor zone in which the unborn baby was located) drops below a threshold.

The threshold may comprise a static amplitude measure or a variable value. For example, if the amplitude of the measured fetal sensor data drops below a particular predetermined value, the sensor system 100 can redetermine the location of the unborn baby 210 within the womb 200. In contrast, in at least one implementation, the sensor system can redetermine the baby's location when the measured fetal sensor data drops a certain percentage. For example, the sensor system may redetermine the location of the unborn baby if the signal strength detected by sensor module 120c drops by 80%.

Further, in at least one implementation, the threshold for redetermining the location of the unborn baby can be set each time the baby's location is redetermined. For example, when determining the sensor zone 220(a-d) that contains the unborn child 210, the sensor system 100 can record the strength of the sensor reading coming from each of the sensor modules 120(a-d). The sensor module with the highest signal strength (e.g., sensor module 120c) may be used to determine the location of the unborn baby 210 within the mother's womb 200. The sensor module with the second highest signal strength (e.g., sensor module 120b) can then be used to set a threshold for redetermining the unborn baby's location. In particular, the second highest amplitude of the signal strength detected by a sensor module (e.g., 120c) may be set as the threshold at which the unborn baby's location should be redetermined. As such, when the signal strength drops from the previously detected highest signal strength to a particular level below the second highest detected signal strength, the sensor system 100 can redetermine the baby's location within the womb 200.

In one or more implementations, the sensor system 100 can store the tracked location of the unborn child 210. The stored data can be accessed and analyzed to identify patterns in the baby's movement. For example, an alarm may be indicated if the baby 210 appears to have grown uncharacteristically inactive. In at least one implementation, the sensor system can also comprise a vibrator that activates as an alarm. The vibrator may alert the mother of a potential problem and/or stimulate the unborn baby 210 to move.

Additionally, the data relating to the baby's location can also be analyzed in conjunction with the data relating to the baby's movements (as detected by the accelerometer sensors). The two data sets together may be used to more fully refine not just the baby's location within the womb 200, but also the baby's position within the womb 200 (e.g., facing front, facing back, upside down, etc.). For example, the combination of data detecting a kick at sensor 120a and the baby's location within sensor zone 200d may be used to determine the baby's position within the womb 200.

For example, an ECG electrode associated with sensor module 120a may detect a large muscle movement. Additionally, an accelerometer associated with sensor module 120a or any other portion of the sensor system 100 may not detect any movement. The lack of movement detected by the accelerometer is an indication that the mother did not move. In such a case, the detected movement from the ECG electrode and the lack of movement by the accelerometer indicates that the baby kicks in zone 220a. The combination of a kick in zone 220a and a heartbeat in zone 220c provides an indication of not only the unborn baby's location within the womb 200 but also the unborn baby's position and orientation within the womb (e.g. feet in zone 220a and torso in zone 220c).

In addition to the sensors disclosed above, implementations of the sensor system 100 can also comprise sensors for measuring contractions, sensors for measuring blood flow within the pregnant mother, sensors for measuring blood pressure within the pregnant mother, capacitance sensor for detecting movement and location of the unborn child, and various other sensors. For example, the sensors for measuring contractions may be capable of measuring Braxton Hicks contractions and/or determining, based upon measured contractions, when the pregnant mother should go to a delivery center. In at least one implementation, the sensors for measuring contractions can comprise a tocodynamometer. The readings received by the sensors for measuring contractions can be processed within the sensor system 100 or can be transmitted to an external computing device for processing.

Similarly, in at least one implementation, the pulse-oximeter sensor may be capable of measuring blood flow and/or blood pressure. The ability to detect changes in the direction of blood flow and/or blood pressure may provide the sensor system 100 with sufficient data to also detect the possible presence of preeclampsia. The ability to detect this condition in its early stages may provide significant health benefits to both the unborn baby and the pregnant mother.

Figure 3:
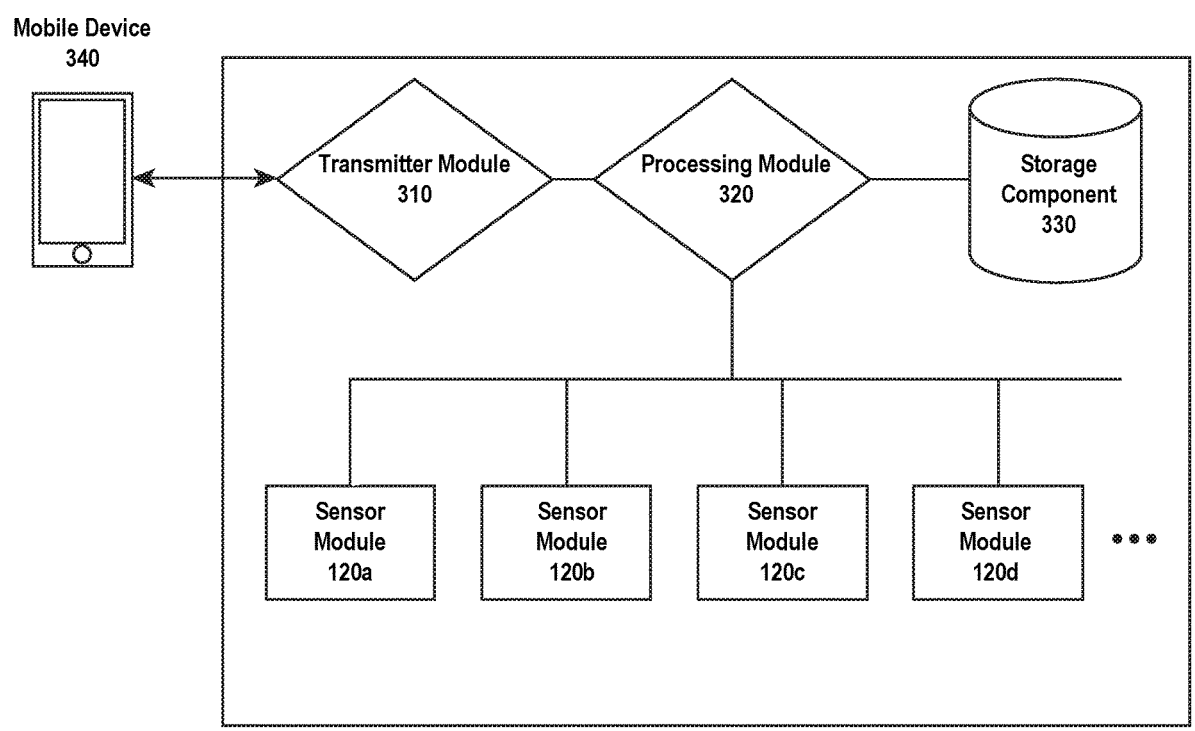
FIG. 3 depicts a schematic diagram of an embodiment of a computer system that includes a sensor system and a mobile computing device.

FIG. 3 depicts a schematic diagram of a computer system that includes a sensor system 100 and a mobile computing device 340. One will understand that the mobile computing device 340 is provided for the sake of example and is generally representative of a computing device. The depicted sensor system 100 comprises various exemplary modules and components configured to gather sensor data and process the data.

For example, the sensor system 100 comprises a transmitter module 310 that is configured to communicate with the mobile device 340. The transmitter module 310 may comprise a WIFI module, a BLUETOOTH module, or some other wired or wireless communication module. The transmitter module 310 may be disposed within the belly-covering garment 140 of FIGS. 1 and 2.

In at least one implementation, the transmitter module 310 is configured to communicate with conventional hospital-based health data monitoring systems. As such, when a pregnant mother arrives at a hospital for delivery, the sensor system 100 can directly communicate with health data equipment within the hospital. The ability to communicate with the hospital equipment may eliminate the need to connect the mother to hospital's own sensor system. Allowing the hospital to receive health data from the sensor system 100 can save time and help the mother to feel more comfortable.

Additionally, in at least one implementation, the transmitter module 310 encrypts the communicated data to ensure privacy. The encryption key may be generated by a user, or may be hardcoded into each individual sensor system 100. For example, there may be an external portion of the sensor system 100 that displays the encryption key (e.g., on a sticker). In this way, a medical professional can quickly access the encryption key without requiring the mother to remember a potential long and complex key.

The sensor system 100 can also comprise a processing module 320 that is in communication with the various sensor modules 120(a-d). The sensor modules 120(a-d) may each comprise various sensors for gathering health data from the unborn baby and the pregnant mother. While only four sensor modules 120(a-d) are depicted, one will understand that the sensor system 100 can comprise any number of sensor modules. In at least one implementation, the processing module 320 gathers data from the sensor modules 120(a-d) and stores the data in the storage component 330. The data storage component 330 may comprise a physical memory module that is disposed within the sensor system 100 within the belly covering garment 140. The processing module 320 can then, either continuously or periodically, transmit the stored data to the mobile device 340 through the transmitter module 310.

In at least one implementation, the data within the storage component 330 is primarily processed by the mobile device 340. In contrast, in at least one implementation, the processing module 320 can also analyze at least a portion of the data within the storage component 330. For example, the processing module 320 can identify negative trends. Additionally, in at least one implementation, the processing module 320 is capable of analyzing the data for the sake of sensor module management, such as the power management features disclosed above.

Figure 4:
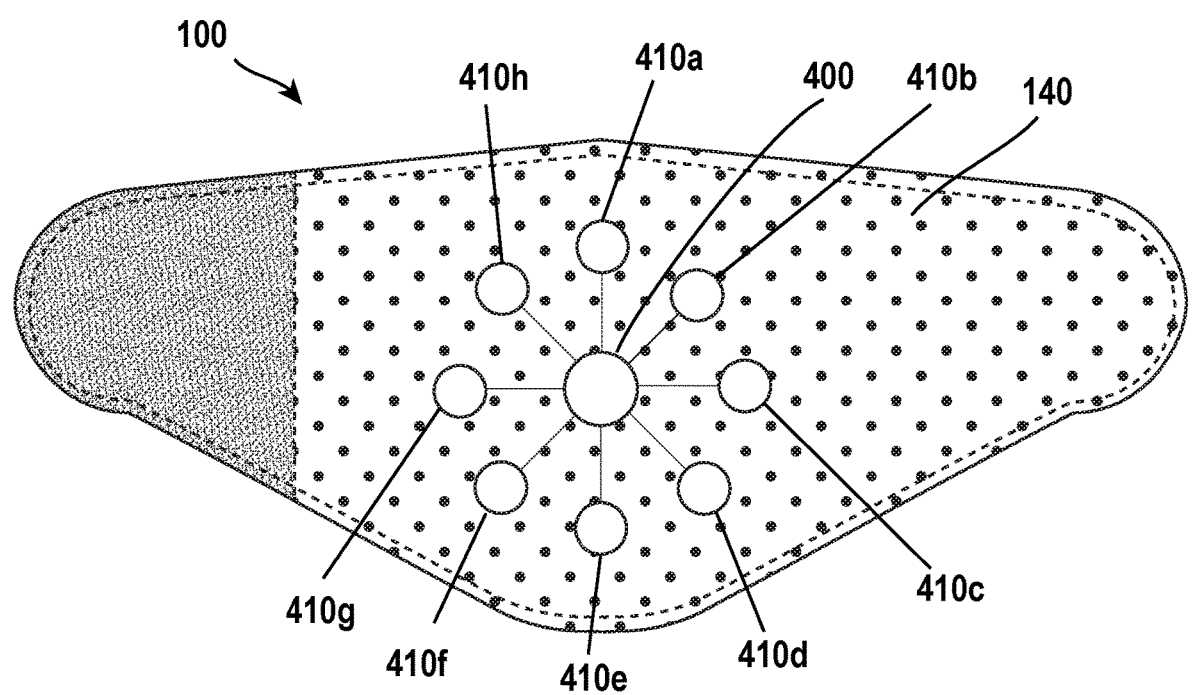
FIG. 4 depicts an embodiment of a belly-covering garment.

FIG. 4 depicts an embodiment of a sensor layout on a belly-covering garment 140. The depicted belly-covering garment 140 comprises a computer chip 400 that is in communication with various sensors 410(a-h). In at least one embodiment, one of the sensors 410(a-h) comprises an ECG electrode. The ECG sensor may comprise a fabric electrode that is connected to the computer chip through conductive thread. The spacing and location of the sensors provides various benefits and features such as locating the fetus with in the mother's womb. Each sensor module 410(a-h) may comprise one or more individual sensors. For example, sensor module 410a may comprise a pulse oximeter, an ECG electrode, a pulse-oximeter, and an accelerometer. In contrast, sensor module 410b may comprise an ECG electrode and a Doppler sensor. Further, in at least one embodiment, the computer chip 400 comprises one or more sensors, such as an accelerometer.

In at least one embodiment, the belly-covering garment 140 is constructed of an elastomeric, or stretchy, material that allows the belly-covering garment 140 to place some tension across the mother's belly 110. The tension assists in holding the sensors tightly in place such that they maintain direct contact with the skin. For example, in at least one embodiment, each ECG electrode (e.g., sensor module 410*h*) comprises a conductive fabric electrode that is configured to contact the belly 110. The fabric electrode may be backed by an elastomeric material, such as foam, that exerts a force on the first electrocardiogram electrode towards the belly 110. In at least one embodiment, the lack of an elastomeric backing can cause the fabric electrode to not be tightly pressed against the belly 110. Instead, natural contours in the belly 110 may cause the fabric electrode to not firmly contact the skin. This may diminish or interfere with signals received from the ECG electrode. Unlike conventional ECG systems which is often positioned by a medical professional while the patient lies in a bed, a wearable ECG system can be worn during normal daily activity. The elastomeric backing provides a solution to the problem of bad connections that arise during normal daily activities which cause the ECG sensor to lose strong contact with the skin.

In at least one embodiment, sensor module 410*c* comprises a ground electrode for the sensor system 100. In at least one embodiment, sensor module 410*c* comprises only a ground electrode. In contrast, sensor module 410*c* may comprise the ground electrode in addition to various sensors such as an accelerometer and/or pulse oximeter. Placing the ground electrode at sensor module 410*c* positions the ground electrode over the user's hip. In at least one embodiment, positioning the ground electrode over the user's hip provides a better ground than other available locations. For example, locating the ground electrode at the hip avoids larger fat and muscle layers that are present in other locations. The fat and muscle layers can interfere with the functioning of the ground plane.

Figure 5:
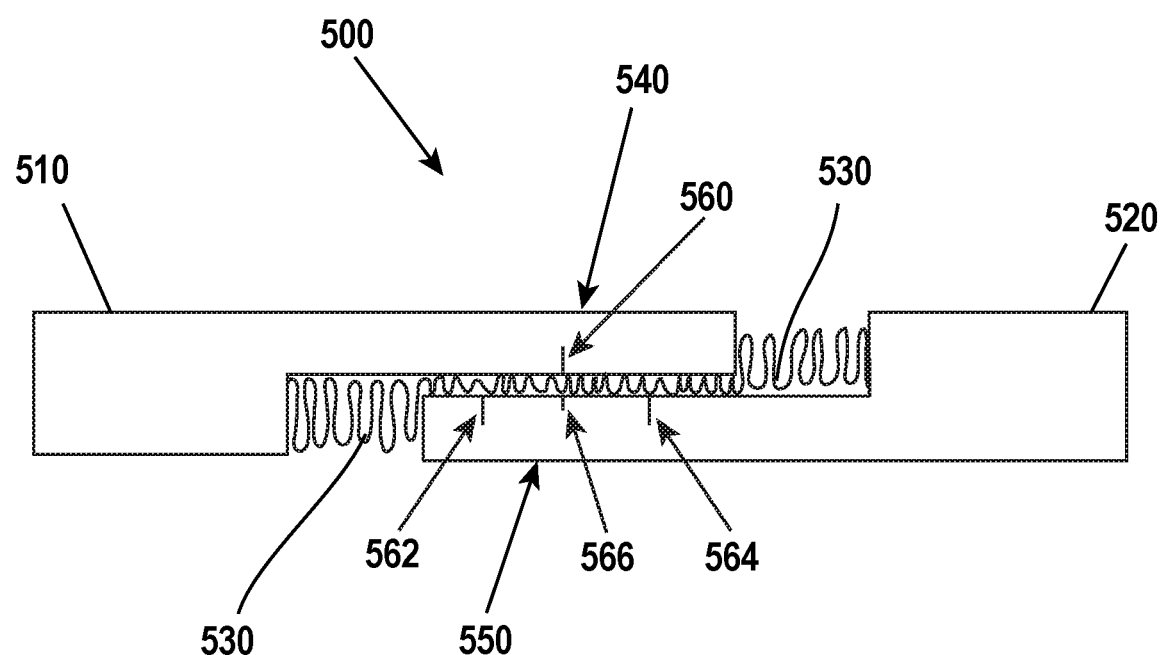
FIG. 5 depicts an embodiment of a built-in strain gauge.

The belly-covering garment 140 also comprises an attachment point that allows a user to tighten or loosen the belly-covering garment 140 as needed. The attachment point may operate through Velcro connectors, clasps, or some other form of connection. FIG. 5 depicts an embodiment of a built-in strain gauge 500 that may be incorporated into the belly-covering garment 140. The depicted built-in strain gauge 500 comprises a left side 510 and a right side 520. Both sides 510, 520 comprise the same material that makes-up the belly-covering garment 140. The built-in strain gauge 500 also comprises elastic attachment portions 530.

The built-in strain gauge 500 also comprises a strain measurement portion 550 and a current strain portion 540. The strain measurement portion 550 comprises marks that indicate "too little tension" 564, "too much tension" 562, and "an acceptable level of tension" 566. The current strain portion 540 comprises a strain indicator 560 that indicates the current tension placed on the belly-covering garment 140. Accordingly, a user can easily adjust the belly-covering garment 140 to the proper tension by utilizing the built-in strain gauge 400.

In at least one embodiment, applying the proper strain to the belly-covering garment 140 positions the sensor modules 120(*a-d*) so that they are in contact with the mother's belly. For example, in at least one embodiment, at least one of the sensor modules 120(*a-d*) comprises an ECG sensor that gathers electrocardiograms from the mother.

As used herein, an ECG gathered from the mother is referred to as a maternal ECG. In at least one embodiment, the processing module 210 filters a fetal ECG out of the maternal ECG, such that ECG data from a fetus can be recovered from ECG data gathered from the mother's belly. The processing module 310 then analyzes both the maternal ECG and the fetal ECG to identify medical trends, health indicators, and any potential concerning indicators.

Further, as described above, at least one of the ECG sensors comprises fabric electrode. The fabric electrode may include a conductive fabric that is coating in silver, stainless steel, aluminum, or any other conductive substance. Additionally, the fabric electrode may be constructed such that it comprises a stretchy characteristic. The stretchy characteristic allows the fabric to be tightly stretched across the mother's belly to ensure a good connection.

In at least one embodiment, if an ECG electrode is not able to detect the fetus, a Doppler sensor is used to find the baby and measure the baby's heartrate. In at various embodiments, the ECG electrode and the Doppler sensor are within the same sensor module or within different sensor modules. Information from the Doppler sensor is then used to reconfigured the ECG sensors to gain a better reading. In the case the ECG reading is still not obtainable, the Doppler sensor can activate periodically to update health readings from the fetus.

In at least one embodiment, the belly-covering garment 140 works in association with additional sensing units, such as a wrist sensing unit, a blood test unit, a scale, an arm cuff, or any number of additional sensing units. In at least one embodiment, the processing module 320 may reside within the belly-covering garment 140 and operate in conjunction with sensors in the various additional sensing units. For example, sensors and processing units within the belly covering garment may access weight information from a connected scale that the mother stands on. Similarly, a wrist sensing unit may provide vital signs from the mother to the belly-covering garment 140. In such a case, the belly-covering garment 140 is able to leverage the vital signs received from the wrist sensing unit to filter out the fetus's vital signs. For instance, the belly-covering garment 140 may detect heart rate signs from both the mother and the fetus. To assist in isolating the heart rate of the fetus from the mother's heart rate, the belly-covering garment 140 may use the heart rate data received from the wrist sensing unit to filter out the mother's heart rate.

Additionally, in at least one embodiment, one or more individual modules 120(*a-d*) from the belly-covering garment may be removable. For example, a Doppler sensor may be interchangeable between the belly-covering garment 140 and an arm cuff. Further, a sensing module may be interchangeable between different belly-covering garment configurations. For example, the same sensor unit may be interchangeable between different locations on the belly-covering garment 140.

One will appreciate that embodiments disclosed herein can also be described in terms of flowcharts comprising one or more acts for accomplishing a particular result. For example, FIG. 6 and the corresponding text describe acts in various systems for performing methods and/or stand-alone methods for monitoring fetal health data and/or mother health data. The acts of FIG. 6 are described below.

Figure 6:
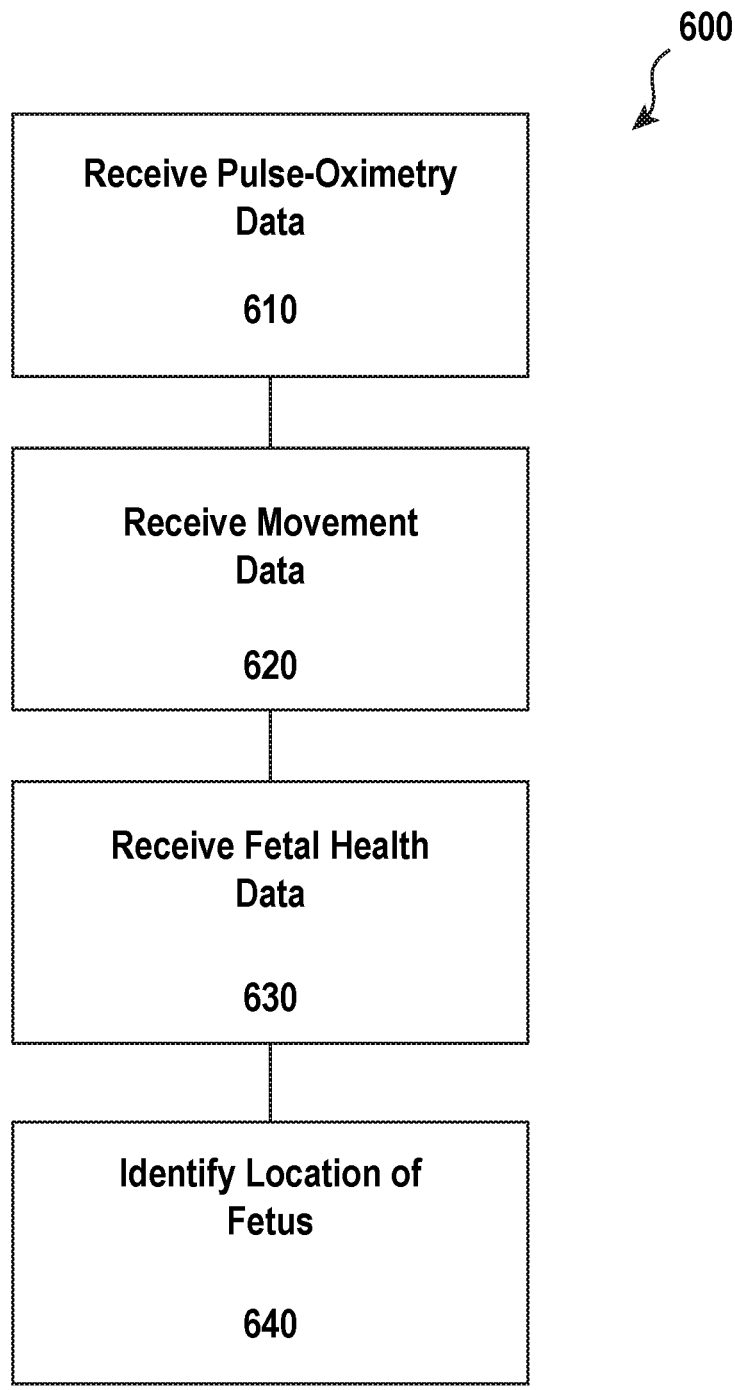
FIG. 6 illustrates a flowchart for an embodiment of a method for monitoring fetal health data and/or mother health data.

FIG. 6 illustrates a flowchart for an embodiment of method 600 for monitoring fetal health data and/or mother health data. The method includes an act 610 of receiving pulse-oximetry data. Act 610 comprises receiving, from a pulse-oximeter sensor, pulse oximetry data from a mother. For example, as depicted and described with respect to FIGS. 1 and 2, a sensor system 100 embedded within a belly-covering garment 110 receives health readings from the mother. The health readings include pulse-oximetry data.

Method 600 also includes an act 620 of receiving movement data. Act 620 comprises receiving, from an accelerometer sensor, movement data from the mother. For example, as depicted and described with respect to FIGS. 1 and 2, a sensor system 100 embedded within a belly-covering garment 110 receives health readings from the mother. One or more of the sensor modules 120(a-d) can comprise an accelerometer that receives movement data from the mother.

Additionally, method 600 includes an act 630 of receiving fetal health data. Act 630 comprises receiving, from a fetal sensor, fetal health data from a fetus within the mother's belly. For example, as depicted and described with respect to FIGS. 1 and 2, a sensor system 100 embedded within a belly-covering garment 110 receives health readings from the unborn baby 210. One or more of the sensor modules 120(a-d) can comprise an ECG or a Doppler sensor that is capable of measuring fetal health data, such a heart rate of the unborn baby 210.

Further, method 600 includes an act 640 of identifying the location of the fetus. Act 640 comprises identifying a relative location of the fetus within the mother's belly using one of more of the pulse oximetry, the movement data, and the fetal health data. Additionally, the pulse-oximeter sensor, the accelerometer sensor, and the fetal sensor are disposed within a belly-covering garment that is configured to at least partially cover the mother's belly and to hold one or more sensor modules directly adjacent to the belly. For example, as depicted and described with respect to FIGS. 1 and 2, different sensor modules 120(a-d) embedded within the belly-covering garment 110 receives health readings from the unborn baby 210. In at least one embodiment, the sensor system 100 filters the mother's heart rate out of a heart rate detected from the unborn baby 210. The sensor system 100 then determines which ECG electrode is receiving the strongest reading of the unborn baby's heart rate. The baby's location and orientation within the womb 200 can then be identified by distinguishing detected kicks from movements of the mother using the techniques described above.

Although the subject matter has been described in language specific to structural features and/or methodological acts, it is to be understood that the subject matter defined in the appended claims is not necessarily limited to the features or acts described above, or the order of the acts described above. Rather, the described features and acts are disclosed as example forms of implementing the claims.

Embodiments of the present invention may comprise or utilize a special-purpose or general-purpose computer system that includes computer hardware, such as, for example, one or more processors and system memory, as discussed in greater detail below. Embodiments within the scope of the present invention also include physical and other computer-readable media for carrying or storing computer-executable instructions and/or data structures. Such computer-readable media can be any available media that can be accessed by a general-purpose or special-purpose computer system. Computer-readable media that store computer-executable instructions and/or data structures are computer storage media. Computer-readable media that carry computer-executable instructions and/or data structures are transmission media. Thus, by way of example, and not limitation, embodiments of the invention can comprise at least two distinctly different kinds of computer-readable media: computer storage media and transmission media.

Computer storage media are physical storage media that store computer-executable instructions and/or data structures. Physical storage media include computer hardware, such as RAM, ROM, EEPROM, solid state drives ("SSDs"), flash memory, phase-change memory ("PCM"), optical disk storage, magnetic disk storage or other magnetic storage devices, or any other hardware storage device(s) which can be used to store program code in the form of computer-executable instructions or data structures, which can be accessed and executed by a general-purpose or special-purpose computer system to implement the disclosed functionality of the invention.

Transmission media can include a network and/or data links which can be used to carry program code in the form of computer-executable instructions or data structures, and which can be accessed by a general-purpose or special-purpose computer system. A "network" is defined as one or more data links that enable the transport of electronic data between computer systems and/or modules and/or other electronic devices. When information is transferred or provided over a network or another communications connection (either hardwired, wireless, or a combination of hardwired or wireless) to a computer system, the computer system may view the connection as transmission media. Combinations of the above should also be included within the scope of computer-readable media.

Further, upon reaching various computer system components, program code in the form of computer-executable instructions or data structures can be transferred automatically from transmission media to computer storage media (or vice versa). For example, computer-executable instructions or data structures received over a network or data link can be buffered in RAM within a network interface module (e.g., a "NIC"), and then eventually transferred to computer system RAM and/or to less volatile computer storage media at a computer system. Thus, it should be understood that computer storage media can be included in computer system components that also (or even primarily) utilize transmission media.

Computer-executable instructions comprise, for example, instructions and data which, when executed at one or more processors, cause a general-purpose computer system, special-purpose computer system, or special-purpose processing device to perform a certain function or group of functions. Computer-executable instructions may be, for example, binaries, intermediate format instructions such as assembly language, or even source code.

Those skilled in the art will appreciate that the invention may be practiced in network computing environments with many types of computer system configurations, including, personal computers, desktop computers, laptop computers, message processors, hand-held devices, multi-processor systems, microprocessor-based or programmable consumer electronics, network PCs, minicomputers, mainframe computers, mobile telephones, PDAs, tablets, pagers, routers, switches, and the like. The invention may also be practiced in distributed system environments where local and remote computer systems, which are linked (either by hardwired data links, wireless data links, or by a combination of hardwired and wireless data links) through a network, both perform tasks. As such, in a distributed system environment, a computer system may include a plurality of constituent computer systems. In a distributed system environment, program modules may be located in both local and remote memory storage devices.

Those skilled in the art will also appreciate that the invention may be practiced in a cloud-computing environment. Cloud computing environments may be distributed, although this is not required. When distributed, cloud computing environments may be distributed internationally within an organization and/or have components possessed across multiple organizations. In this description and the following claims, "cloud computing" is defined as a model for enabling on-demand network access to a shared pool of configurable computing resources (e.g., networks, servers, storage, applications, and services). The definition of "cloud computing" is not limited to any of the other numerous advantages that can be obtained from such a model when properly deployed.

A cloud-computing model can be composed of various characteristics, such as on-demand self-service, broad network access, resource pooling, rapid elasticity, measured service, and so forth. A cloud-computing model may also come in the form of various service models such as, for example, Software as a Service ("SaaS"), Platform as a Service ("PaaS"), and Infrastructure as a Service ("IaaS"). The cloud-computing model may also be deployed using different deployment models such as private cloud, community cloud, public cloud, hybrid cloud, and so forth.

Some embodiments, such as a cloud-computing environment, may comprise a system that includes one or more hosts that are each capable of running one or more virtual machines. During operation, virtual machines emulate an operational computing system, supporting an operating system and perhaps one or more other applications as well. In some embodiments, each host includes a hypervisor that emulates virtual resources for the virtual machines using physical resources that are abstracted from view of the virtual machines. The hypervisor also provides proper isolation between the virtual machines. Thus, from the perspective of any given virtual machine, the hypervisor provides the illusion that the virtual machine is interfacing with a physical resource, even though the virtual machine only interfaces with the appearance (e.g., a virtual resource) of a physical resource. Examples of physical resources including processing capacity, memory, disk space, network bandwidth, media drives, and so forth.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

We claim:

1. A sensor system for monitoring fetal health data and/or mother health data, comprising:
   a belly-covering garment, wherein the belly-covering garment is configured to at least partially cover a belly and to hold one or more sensor modules directly adjacent to the belly;
   the one or more sensor modules disposed at particular locations within the belly-covering garment, wherein the one or more sensor modules comprise:
      a maternal-heart rate sensor configured to gather pulse oximetry data from a mother through contact with the belly,
      an accelerometer sensor configured to gather movement data from the mother, and
      a fetal sensor module configured to gather fetal health data from a fetus within the belly;
   the fetal sensor module comprising one or more processors and multiple individual sensor units that are each configured to gather a heart rate from the fetus;
   the one or more processors are configured to identify a particular individual sensor unit from the multiple individual sensor units that is receiving the strongest heart rate signal;
   after identifying the particular individual sensor unit, the one or more processors are configured to decrease a sampling rate of the other multiple individual sensor units except the particular individual sensor unit, wherein the other multiple individual sensor units continue to gather fetal health data from a fetus within the belly at a lower sampling rate than the particular individual sensor unit;
   in response to identifying the particular individual sensor unit is receiving the strongest heart rate signal, the one or more processors determine a relative location of the fetus within the belly with respect to a location of the particular individual sensor unit, and
   redetect, with the one or more processors, the relative location of the fetus when a strength of the heart rate signal received by the particular individual sensor unit drops below a threshold, wherein the threshold is equal to a signal strength of a second strongest heart rate signal received by another sensor unit at a time that the particular individual sensor unit received the strongest heart rate signal from the fetus.

2. The system as recited in claim 1, wherein the one or more sensor modules comprise individual Doppler sensors.

3. The system as recited in claim 1, wherein the maternal-heart rate sensor and the fetal sensor module comprise a common ECG sensor.

4. The system as recited in claim 1, wherein the maternal-heart rate sensor is configured to measure the heart rate of the mother and the fetal sensor module is configured to measure a heart rate of the fetus, and the one or more processors use the pulse oximetry data from the maternal-heart rate sensor to remove noise in the fetal health data from the fetal sensor module.

5. The system as recited in claim 1, wherein the one or more processors are configured to use data from the accelerometer sensor to detect movements and kicks from the fetus.

6. A method for monitoring fetal health data and/or mother health data, comprising:
   receiving, from a maternal-heart rate sensor, pulse oximetry data from a mother;
   receiving, from an accelerometer sensor, movement data from the mother;
   receiving, from a fetal sensor module, fetal health data from a fetus within a mother's belly, wherein the fetal sensor module comprises multiple individual sensor units that are each configured to gather a heart rate from the fetus;
   identifying a relative location of the fetus within the mother's belly using one or more of the pulse oximetry data, the movement data, and the fetal health data;
   identifying a particular individual sensor unit from the multiple individual sensor units that is receiving the strongest heart rate signal;
   decreasing a sampling rate of the other multiple individual sensor units except the particular individual sensor unit, wherein the other multiple sensor units continue to gather fetal health data from a fetus within the mother's belly at a lower sampling rate than the particular individual sensor unit;
   determining a strength of the heart rate signal received by the particular individual sensor unit drops below a signal strength of a second strongest heart rate signal received by another sensor unit at a time that the particular individual sensor unit received the strongest heart rate signal from the fetus,
   based upon the determination, reidentify the relative location of the fetus; and wherein the maternal-heart rate sensor, the accelerometer sensor, and the fetal sensor module are disposed within a belly-covering garment that is configured to at least partially cover the mother's belly and to hold one or more sensor modules directly adjacent to the mother's belly.

7. The method as recited in claim 6, wherein one or more of the maternal-heart rate sensor, the accelerometer sensor, and the fetal sensor module are disposed within an array of sensors spread across at least one axis of the mother's belly.

8. The method as recited in claim 7, wherein the fetal sensor module comprises a Doppler sensor.

9. The method as recited in claim 7, wherein the fetal sensor module comprises a microphone sensor.

10. The method as recited in claim 6, further comprising:
   measuring, with the maternal-heart rate sensor, a heart rate of the mother;
   measuring, with the fetal sensor module, a heart rate of the fetus; and
   calculating a filtered heart rate of the fetus by subtracting the measured heart rate of the mother from the measured heart rate of the fetus.

11. The method as recited in claim 6, further comprising:
   detecting a presence of activity from an electrocardiogram sensor, wherein the electrocardiogram sensor is in contact with the mother's belly;
   detecting a lack of movement from the accelerometer sensor; and
   determine a fetal movement has occurred based upon the presence of the activity from the electrocardiogram sensor and the lack of movement detected by the accelerometer sensor.

12. A computing system for monitoring fetal health data and/or mother health data, comprising:
   a garment that is configured to at least partially cover a belly and to hold a plurality of sensor modules directly adjacent to the belly;
   the plurality of sensor modules disposed individually as an array of sensor modules configured to be spread across the belly;
   a first sensor module comprising a first electrocardiogram electrode that is configured to gather first fetal heartbeat data, wherein the first sensor module is associated with a first region of the belly;
   a second sensor module comprising a second electrocardiogram electrode that is configured to gather second fetal heartbeat data, wherein the second sensor module is associated with a second region of the belly that is different than the first region; and
   wherein the computing system is configured to:
      determine whether a fetus is within the first region or the second region based upon readings received from the first sensor module and the second sensor module,
      identify that the first sensor module is receiving a strongest fetal heart rate signal, and
      decrease a sampling rate of the second sensor module, wherein the second sensor module continues to gather fetal health data from a fetus within the belly at a lower sampling rate than the second sensor module.

13. The computing system as recited in claim 12, further comprising:
   at least one sensor module comprising an accelerometer sensor that is configured to gather movement data from a mother; and
   wherein the computing system is configured to determine a fetal movement has occurred based upon a presence of fetal activity detected by the first electrocardiogram electrode and a lack of movement detected by the accelerometer sensor.

14. The computing system as recited in claim 12, wherein:
   the first electrocardiogram electrode comprises a fabric electrode that is configured to contact the belly; and
   the first electrocardiogram electrode is backed by an elastomeric material that is configured to exert a force on the first electrocardiogram electrode towards the belly.

15. The computing system as recited in claim 12, wherein the garment further comprises a ground electrode configured to be positioned over a hip of a wearer.

16. The system as recited in claim 5, wherein the one or more processors are configured to use accelerometer data to determine a direction that the fetus is facing.

\* \* \* \* \*